United States Patent [19]

Brandt et al.

[11] Patent Number: 4,797,356

[45] Date of Patent: Jan. 10, 1989

[54] MONOCLONAL ANTIBODIES SPECIFIC TO GLACTOSYLTRANSFERASE ISOENZYME II AND THEIR USE IN CANCER IMMUNOASSAYS

[75] Inventors: Alan E. Brandt, Redwood City; Morito Uemura, Menlo Park, both of Calif.

[73] Assignee: Konishiroku Photo Industries, Co., Ltd, Japan

[21] Appl. No.: 803,818

[22] Filed: Dec. 2, 1985

[51] Int. Cl.[4] .................. G01N 33/53; G01N 33/577; G07K 15/14
[52] U.S. Cl. ...................................... 435/7; 435/172.2; 435/240.27; 436/518; 436/533; 436/538; 436/548; 436/813; 530/387
[58] Field of Search ................... 435/7, 172.2, 14, 68, 435/240.27; 436/548, 524, 518, 813, 538, 533; 530/389, 387

[56] References Cited

U.S. PATENT DOCUMENTS 4,460,561  7/1984  Goldenberg ...................... 530/389

OTHER PUBLICATIONS

Podolsky, D. K. et al, Proc. Natl. Acad. Sci. USA (1984), 81:2529–2533.
Chatterjee, S. K., et al, Cancer Res. (1984), 44:5725–5732.

*Primary Examiner*—Robert J. Warden
*Assistant Examiner*—Florina B. Hoffer
*Attorney, Agent, or Firm*—Ciotti & Murashige, Irell & Manella

[57] ABSTRACT

Murine monoclonal antibodies specific to the tumor marker galactosyltransferase II (GT-II) which have no measurable cross-reactivity with galactosyltransferase I (GT-I) are described. These antibodies are used in assays to determine levels of GT-II ikn serum or other body fluid samples, which levels, depending on their magnitude, are indicators of cancer.

11 Claims, No Drawings

MONOCLONAL ANTIBODIES SPECIFIC TO GLACTOSYLTRANSFERASE ISOENZYME II AND THEIR USE IN CANCER IMMUNOASSAYS

DESCRIPTION

1. Technical Field

This invention is in the fields of immunology and cancer diagnosis and monitoring. More particularly it relates to monoclonal antibodies specific to the tumor marker galactosyltransferase isoenzyme II (GT-II) and to immunoassays for GT-II.

2. Background Art

Galactosyltransferases (GT) are enzymes that catalyze the transfer of galactose from UDP-galactose to the nonreducing residues of oligosaccharides of various glycoproteins as well as monosaccharides. Abnormal GT activity has been observed in a variety of malignant tissues leading prior workers to investigate GT as a serological marker of malignancy. Total serum GT was found to be a poor indicator of malignancy. Serum levels of the GT isoenzyme, GT-II, however, have been found to correlate well with the presence of cancer. GT-II represents a small proportion of the total serum GT. An electrophoretically distinct (faster migrating) species, called galactosyltransferase I (GT-I), constitutes the major proportion of serum GT.

Murine monoclonal antibodies to GT have been reported previously. Podolsky, D. K., and Isselbacher, K. J., *PNAS (USA)* (1984) 81: 2529-2533, describe the synthesis of seven murine anti-GT monoclonal antibodies, one of which was found to be "relatively" specific to GT-II. The data presented for that antibody show that it has significant cross-reactivity to GT-I and IgG. The antibody also exhibited only moderate to low affinity. Such cross-reactivity and low affinity limits the usefulness of this antibody as an assay reagent for diagnosing cancer. Chatterjee, S. K., et al, *Cancer Res* (1984) 44: 5725-5732, report five murine anti-GT monoclonal antibodies that have high affinity. No indication is given, however, regarding the isoenzyme specificity of these antibodies or their practical usefulness as reagents for diagnosing cancer.

The present invention provides a murine anti-GT-II monoclonal antibody of high affinity that does not cross-react with GT-I or IgG. This antibody is an excellent immunoassay reagent for determining GT-II levels in serum or other body fluids in which GT appears.

DISCLOSURE OF THE INVENTION

The present invention provides a monoclonal antibody that is specific to GT-II, a hybridoma that produces the antibody and immunoassay methods and reagents for determining the level of GT-II in body fluids.

Accordingly, one aspect of the invention is a monoclonal antibody to galactosyltransferase II that does not cross-react with galactosyltransferase I.

Another aspect of the invention is a hybridoma line that produces such an antibody.

Another aspect of the invention is an article of manufacture for use in an immunoassay for galactosyltransferase II comprising the monoclonal antibody of claim 1 bound to a solid support.

Another aspect of the invention is an assay for human cancer comprising (a) incubating a sample of body fluid from a patient with said article of manufacture;

(b) removing unbound body fluid from said support;

(c) determining the level of galactosyltransferase activity exhibited by the material bound to the support.

MODES FOR CARRYING OUT THE INVENTION

As used herein the term "monoclonal antibody" refers to an immunoglobulin composition having a substantially homogeneous population of antibodies, each of which binds to the same antigenic determinant. Unless otherwise indicated, the term is not intended to be limited to antibodies of any particular mammalian species or isotype or to antibodies prepared in any given manner. The term is intended to include whole antibody molecules as well as antigen-binding fragments (e.g., Fab, F(ab')$_2$, Fv).

As used herein the term "hybridoma line" refers to individual cells, harvested cells, and cultures containing cells so long as they are derived from cells of the cell line referred to.

As used herein with respect to hybrid cell lines the term "progeny" is intended to include all derivatives, issue, and offspring of the cell lines regardless of generation or karyotypic identity.

As used herein the terms "specific to GT-II" and "GT-II specific" refer to monoclonal antibodies that immunoreact with (bind to) GT-II but do not cross-react with GT-I or other components of serum, except possibly with oligomeric forms of GT-II. Such antibodies bind to determinants that are present in GT-II (or GT-II oligomers) but are not present in GT-I or other serum components. The GT-II specific monoclonal antibody designated 3872 and functional equivalents thereof (i.e., monoclonal antibodies that bind the same antigenic determinant as 3872) are preferred embodiments.

As used herein the term "body fluid" refers to those body fluids in which GT is found. It includes, without limitation, blood, blood components such as plasma and serum, ascites fluid, tissue culture supernatants, and spinal fluid. Serum is preferred.

The general process used to prepare hybridoma cell lines that secrete GT-II specific monoclonal antibodies is as follows. A preparation containing human GT, including GT-II, is used to immunize subject animals to obtain a source of lymphocytes which are capable of secreting antihuman GT antibodies. Ordinarily, the subject animal, such as a rat or mouse or larger mammal, is injected intraperitoneally or intravenously with the GT preparation, usually in conjunction with an adjuvant, and permitted to mount an immune response. Suitable lymphocytes are obtained either from the circulatory system (peripheral blood lymphocytes (PBLs)) or, if the animal can be sacrificed, from the spleen. The spleen cells or PBLs are then fused with an immortalizing cell line to obtain hybridomas.

In a typical fusion, the lymphocyte preparation is mixed with a culture of an immortalizing cell line, usually from the same species as the immunized animal such as, where appropriate, a murine or rat myeloma. However, other methods of immortalization are possible, such as transformation with an immortalizing virus such as the Epstein-Barr virus. In the fusion, the preparations of antibody-producing lymphocytes and immortalizing cells are mixed in the presence of a fusogen, most commonly polyethylene glycol, and plated out into a selective medium. The most commonly used selective medium is hypoxanthine-aminopterinthymidine (HAT) medium, which permits survival of only those cells containing a bypass pathway for synthesis of nucleic acids, which most lymphocytes have but most immortalizing cell lines lack. Therefore, in the HAT medium the immortalizing myeloma cell lines will die (due to the their lack of the bypass); unhybridized lymphocyte cell lines will die simply because they are not immortalized. Only hybridomas will survive, as they share the common features of immortality and the presence of the bypass pathway. The selection medium needs, of course, to be chosen to correspond to the metabolic characteristics of the immortalizing fusion partner.

Surviving cultures, after a suitable time period in the selection medium, are spread onto microtiter plates and screened for the production of anti-GT antibody. Because of the unavailability of pure GT-II, it is convenient to screen the supernatants against a total GT mixture followed by screening against GT-I. Samples that are positive against the mixture and negative against GT-I are GT-II specific. A variety of immunoassay techniques are available for screening, including radioimmunoassay and enzyme immunoassay techniques. In a typical procedure, microtiter plates are coated with the antigen preparation, washed, incubated with various dilutions of the hybridoma supernatants to be tested, washed again, and then treated with a labeled antibody prepared against the species of origin of the expected antibody. Only wells where the monoclonal antibodies have been retained by the antigen preparation will be labeled by the second antibody. Variations of this method are, of course, possible, and, indeed, common.

Suitable hybridoma colonies which are shown to secrete GT-II specific antibodies are then subcultured by successive transfers until is is clear that a single "monoclonal" cell line is present. Such cultures can then be maintained indefinitely and cultured under suitable conditions to obtain the desired supplies of the GT-II specific monoclonal antibody. Alternatively, the hybridomas may be injected into suitable subjects, most commonly mice or rats, to effect an in vivo culturing of the hybridoma by induction of antibody producing tumors. This results in a high concentration of the antibody in the ascites fluid (a peritoneal exudate) as well as in the bloodstream. Of course, the resulting monoclonal antibody preparation is not entirely pure, since the indigenous antibodies of the host will also be present. However, these are present only in minimal amounts, and the desired antibody predominants sufficiently to obtain sufficient purity for most purposes. If desired, the GT-II specific monoclonal antibody may be isolated from culture media or body fluids, as the case may be, by conventional immunoglobulin purification procedures, such as ammonium sulfate precipitation, gel electrophoresis, dialysis, chromatography, and ultrafiltration. Antibodies of IgG isotype are preferred because they are easy to isolate.

The GT-II specific monoclonal antibodies of the invention are used in immunoassays to detect levels of GT-II in body fluids, typically serum. Elevated levels of GT-II in the fluid indicate the presence of cancer. In this regard, normal plasma or serum (i.e., plasma or serum from a patient that does not have cancer) will typically exhibit a GT-II enzyme activity of about 30 to 175 picomoles/hr/ml, whereas plasma/serum from cancer patients will usually have a GT activity greater than about 175 picomoles/hr/ml (measured using ovalbumin as a substrate). (The specific activity of pure GT-II is approximately 500 μmoles/hr/mg.) The extent of elevation may vary with the particular type of cancer and the particular fluid assayed. Elevated amounts of GT-II are associated with a variety of cellular neoplasms including carcinomas (such as ovarian tumors), melanomas, leukemias, and lymphomas. Assays involving these antibodies are thus useful in diagnosis as in screening programs for early detection of cancer, in therapy as in evaluating the status of the disease after surgical, radiation or chemical treatment, or in prognosis such as in detecting the possibility of recurrence or metastasis.

While many conventional immunoassay protocols may be used, a preferred protocol involves the steps of incubating the body fluid sample with immobilized GT-II specific monoclonal antibody, removing unbound material, and determining GT activity possessed by the solid (immobilized) phase. The antibody may be immobilized on appropriate solid supports or substrates such as microtiter plate wells or beads by adsorption or covalent bonding. Incubation with the body fluid sample is carried out under conditions that favor binding of any GT-II in the sample to the immobilized antibody. In this regard it is preferable that the antibody have an affinity of at least about $10^9$, and preferably $10^{10}$, L/M (determined by Scatchard analysis) to provide sufficiently strong antibody-antigen binding. Physiological conditions (pH, ionic strength, temperature) will normally be used for the incubation. Following the incubation the unbound body fluid is removed from the solid phase and the solid phase is washed to remove residual body fluid. GT activity of the solid phase is then assessed by conventional procedures known in the art.

EXAMPLES

The following examples illustrate specific embodiments of the various aspects of the invention. These examples are not intended to limit the invention in any manner.

The following describes the preparation, identification, and characterization of GT-II specific monoclonal antibodies. The strategy used for preparing and isolating GT-II specific monoclonal antibodies was to immunize BALB/c mice with a GT mixture obtained from human malignant tumor effusion fluid, prepare hybridomas via cell fusion between immunized mouse spleen cells and a mouse myeloma cell line, and screen the resulting hybridomas for secretion of antibody against the mixture of GT. The cultures identified as secreting antibody against the GT mixture obtained from human malignant tumor effusion fluid are then checked for reactivity with GT-I isolated from normal human serum. Those hybridomas which were positive against the tumor fluidderived GT but negative toward normal GT-I are considered to be GT-II specific.

PREPARATION OF GT ANTIGEN

Human tumor effusion fluid was obtained from patients with ovarian tumors. In addition, tumor effusion fluid from a patient with a malignant kidney tumor was obtained as was outdated normal human serum. All human fluids were stored frozen at −80° C. and thawed at 4° C. prior to use.

A rapid, three-step purification procedure was developed for GT purification and applied to both normal serum and tumor effusion fluid GT purification. All GT purification procedures were performed at 4° C.

The thawed GT-containing human fluid samples were dialyzed overnight against 20 volumes of cold distilled water and adjusted to 10 mM sodium cacodylate, 10 mM $MnCl_2$. 5 mM N-acetylglucosamine (GlcNAc), and 100 μM phenylmethylsulfonylfluoride (PMSF). After standing for one hour, the solution was centrifuged at 16,300×g for 30 min. The supernatant was removed and an aliquot reserved for GT activity determination (described below). The pellet was discarded.

The supernatant was applied to an α-lactalbumin-Sepharose 4B affinity column (5×30 cm) and the column washed with 10 mM sodium cacodylate, 10 mM $MnCl_2$, 5 mM GlcNAc, 50 μM PMSF, 0.005% Triton X-100 (pH 7.2) (buffer A). After all unbound protein was eluted, GT was specifically eluted with buffer A lacking GlcNAc and collected in tubes containing sufficient 1M GlcNAc so that the final GlcNAc concentration was 5 mM. GT-containing fractions were pooled and rechromatographed on a second α-lactalbumin affinity column (1.5×28 cm) under conditions identical to the first α-lactalbumin column. After elution of all unbound protein, GT was eluted with GlcNAc-free cacodylate buffer into sialanized tubes containing sufficient GlcNAc so that the GlcNAc concentration is restored to 5 mM.

GT-containing fractions were combined and passed through a goat antihuman IgG affinity column (1.5×3 cm) (Sigma Chemical Co.) previously equilibrated with buffer A. GT-containing fractions were pooled, placed in dialysis tubing, and concentrated to approximately 10 ml using Aquacide II (Calbiochem). GT was dialyzed against distilled water and further concentrated to 0.2 ml using an Isco Electrophoretic Concentrator.

ASSAY OF GT ACTIVITY

UDP-[$^3$H]galactose (40.3 Ci/mmol) was obtained from New England Nuclear and a 2 mM solution was prepared by diluting the UDP-[$^3$H]galactose with unlabeled UDP-galactose (Sigma Chemical Co.). The specific activity was determined from the optical density of an appropriately diluted aliquot at 262 nm and liquid scintillation counting. The final specific activity was approximately $3 \times 10^6$ cpm/μmol. In some instances, higher specific activity ($6 \times 10^7$ cpm/μmol, 0.4 mM) UDP-[$^3$H]galactose was utilized.

GT activity was determined by combining 7 μl of 2 mM UDP-[$^3$H]galactose, 3 μl of 0.2M $MnCl_2$, 50 μl of ovalbumin solution (50 mg/ml in 0.1M sodium cacodylate, 0.154M sodium chloride, pH 7.4) and 10 μl of enzyme containing sample at 0° C. After mixing, the assay tubes are incubated at 37° C. for 1 hr and then placed at 0° C. Aliquots (50 μl) are removed, spotted on one-inch squares of Whatman 3-mm paper, and immediately placed in 10% trichloroacetic acid (TCA) at room temperature. After washing the assay papers 3 to 4 times in 10% TCA (10 min each wash), excess TCA is removed by washing with 95% ethanol (10 min) and ether (10 min) before drying. The amount of acid-precipitated [$^3$H]galactose is quantitated using liquid scintillation techniques.

Occasionally other protein substrates were used as GT substrates. When this was done, TCA solutions were replaced by 5% phosphotungstic acid containing 2N HCl. All othe procedures were as described above.

Polyacrylamide Gel Electrophoresis

The purity of isolated proteins was evaluated by sodium dodecylsulfate polyacrylamide gel electrophoresis (SDS-PAGE). GT isoenzymes were separated using an 8% polyacrylamide gel under nondenaturing conditions (Podolsky and Weisner. *Biochem Biophys Res Commun* (1975) 65: 545–551). To measure GT activity following nondenaturing PAGE, individual sample lanes were cut into 2.5 mm sections and soaked in elution buffer as described by Podolsky and Weisner (*J Biol Chem* (1979) 254: 3983–3990). Eluted GT was assayed as described above using the high specific activity UDP-[$^3$H]galactose. Proteins were visualized following PAGE using a sensitive silver staining procedure. "Western" blotting of PAGE separated GT onto nitrocellulose was performed. GT prepared from normal human serum showed only one protein-staining band with a migration typical of GT-I. Preparations from human malignant tumor effusion fluid showed the same GT-I band, but in addition, a major band corresponding to GT-II is also observed. Confirmation that both bands contain galactosyltransferase activity was obtained by slicing the gel into 2.5 mm segments and assaying for galactosyltransferase activity. GT activity is clearly associated with both protein bands.

Several of the main human malignant tumor effusion fluid GT preparations contained small quantities of protein-staining material which migrated slower than GT-II on nondenaturing PAGE. These higher molecular weight protein bands were not observed in GT isolated from normal human serum. A graph of the relative migration of the bands vs log M.W. (assuming a monomer molecular weight of 57,000 and each observed band as a multimer of the monomer) produced a straight line—strongly suggesting that the additional bands which are observed are due to oligomer formation in the GT preparation. No oligomer bands have been observed in any GT preparations from normal human serum. Hence, it appears GT-II most probably contains a structural element that causes a self-association and that this structure is absent in GT-I. This structural difference could form the basis for a unique immunological epitope in GT-II which could distinguish it from GT-I.

Immunization Protocol

BALB/c mice were immunized with approximately 30 μg of GT per mouse in complete Freund's adjuvant (approximately 7.5 μg in each flank and 15 μg intraperitoneally (ip). Three weeks later, each animal received a booster of 30 μg GT in incomplete Freund's adjuvant ip. Two weeks after the booster, antibody-containing serum was prepared following ocular eye bleeds. This serum was checked for the presence of antibody using an enzyme-linked immunosorbent assay (ELISA). If the serum is antibody-positive, the mice receive 50 μg of GT in phosphate-buffered saline (PBS) intravenously (iv). Three days following the iv boost, the animals were sacrificed, the spleens removed, and cell fusions performed as described below.

ELISA

The wells of 96-well microtiter plates were coated with purified GT (50 μl, 5 μg/ml, 0.05M sodium carbonate, pH 9.6) overnight at 4° C. After removing the GT solution, the wells are washed once with 0.1% Tween 80 in phosphate (0.01M) buffered saline (0.15M sodium chloride), pH 7.4 (PBS). The wells are then filled with 3% bovine serum albumin (BSA) in PBS and either incubated overnight at 4° C. or 1 hr at 37° C. The BSA solution is removed and the well exhaustively washed with 0.1% Tween 80 in PBS. Antibody-containing solution (50 μl, diluted in 1% BSA in PBS) is added and incubated at 37° C. for 1 hr. The wells are exhaustively washed with 0.1% Tween 80 in PBS and 50 μl peroxidase-conjugated goat antimouse IgG+IgM (Tago Immunodiagnostics; diluted in 10% normal goat serum in PBS). After incubation at 37° C. for 1 hr, the antibody solution is removed and the wells extensively washed with 0.1% Tween 80 in PBS. Peroxidase substrate solution [100 μl per well; 0.5M citric acid, 0.25 mM 2,2' azino-bis(3-ethylbenzthiazoline sulfonic acid) and 0.01% hydrogen peroxide] is added and the color allowed to develop. The optical density at 410 nm is determined using a MR 580 Microelisa Auto Reader (Dynatech).

Growth of Myeloma Cells

SP2/O-Ag 14 cells were grown in RPMI 1640 tissue culture media containing 10% fetal calf serum and supplemented with glutamine, penicillin, and streptomycin (growth medium). Myeloma cells were grown in T75 tissue culture flasks to a density of $7-8 \times 10^5$ cells/ml. Cell viability was determined by trypan blue dye exclusion and counting using a hemocytometer.

Cell Fusion

Spleens from immunized mice are gently homogenized in 3 ml of growth medium and the spleen cells isolated by centrifugation at $200 \times g$. After washing the spleen cells three times with serum-free RPMI 1640, approximately equal numbers of viable spleen and myeloma cells are combined, mixed, and isolated by centrifugation. The combined cells are gently suspended in 50% polyethylene glycol (PEG) (aldehyde-free, BRL Laboratories) in RPMI 1640 and gradually diluted with RPMI 1640 until the PEG concentration is 5%. The cells are isolated by centrifugation, gently dispersed in growth medium, seeded at $10^6$ cells/0.1 ml/well into microtiter plate wells, and the cells incubated at 37° C. in 5% $CO_2$. One day after cell fusion, 0.1 ml of HAT medium (growth medium supplemented with 0.01 mM hypoxanthine, 1.6 μM thymidine, and 0.04 μM aminopterin) is added. Every 2 to 3 days thereafter, approximately half of the HAT medium is removed and replaced with fresh HAT medium. The cells are observed with a microscope. Clones appear at 7 to 10 days, and by 10 to 14 days culture supernatants are screened by the GT ELISA assay for anti-GT antibody secretion. Positive antibody-secreting colonies are expanded into 24-well plates followed by transfer to T-25 flasks when the cell density becomes high. Hybridomas are maintained on HT medium (HAT medium lacking aminopterin) and checked for anti-GT antibody secretion at all stages.

Sixteen fusions produced 20 hybridomas that produced antibodies that bound to the GT mixture on initial ELISA screening. These hybridomas were subcloned for further evaluation.

Hybridoma Subcloning

Hybridomas secreting anti-GT antibodies are cloned by limiting dilution. Hybridoma cells are suspended at 0.5 viable cells/0.1 ml HT medium and 0.1 ml placed in each well of a microtiter test plate. The cells are grown (about 2 weeks) with media changes every 5 to 7 days. After two weeks, the cells are screened for antibody production using the ELISA. Supernatants from 2 of the 20 hybridomas were found not to cross-react with the normal serum GT (GT-I) and were thus determined to be specific to GT-II. These two hybridomas were designated 3872 and 4562.

Production of Anti-GT Monoclonal Antibody (McAb)

The two GT-II specific hybridomas were grown in cell culture on HAT medium in T-25 and T-75 tissue culture flasks. Hybridoma cells were grown to a density of 5 to $8 \times 10^5$ cells/ml. Hybridoma cells were harvested by centrifugation at $200 \times g$ for 5 min and the supernatant culture fluid reserved for McAb purification or subtyping. For McAb production in mouse ascites fluid, the hybridoma cells are washed once with serum-free RPMI 1640 and resuspended in RPMI 1640 at $1 \times 10^7$ cells/ml. BALB/c mice (treated with pristane (2,6,10,14-tetramethylpentadecane) at least 7 days previously) were injected with 0.5 ml ($5 \times 10^6$ cells) ip. Evidence of an ascites tumor should be obvious within 1 to 2 weeks. When the mice become lethargic and the abdomen is distended, the ascites fluid is harvested, the cells removed by centrifugation ($200 \times g$ for 5 min), and the McAb-containing supernatant carefully removed.

Purification of McAb

Ascites fluid is diluted with 2 volumes of PBS and saturated ammonium sulfate added to 50% saturation. The McAb-containing precipitate is isolated by centrifugation at $10,000 \times g$ for 15 min, and after washing, dissolved in a small volume of PBS and dialyzed against two changes of 100 volumes of 20 mM Tris, 40 mM NaCl buffer (pH 7.8). The McAb is further purified by chromatography on a Mono Q (quarternary ammonium resin, Pharmacia) column utilizing an FPLC apparatus (Pharmacia). McAb is eluted with a linear salt gradient and assayed by ELISA McAb prepared by this method is very highly purified and is suitable for use in GT assay development.

Typing and Subtyping McAb

The antibody class and subtype of the GT-II specific McAbs was determined on cell culture supernatants via Ochterlony immunodiffusion with commercially available (Miles Laboratories) specific antimouse immunoglobulin antisera. 3872 was found to be an IgG1 and 4562 an IgM. The affinity constant of 3872 was found to be $4 \times 10^{10}$ L/M by Scatchard analysis. A sample of the hybridoma that produces McAb 3872 was deposited at the American Type Culture Collection on 19 November 1985 under accession no. HB 8945. This deposit was made pursuant to the provisions of the Budapest Treaty and will be maintained and access provided thereto in accordance with that Treaty.

Confirmation of Specificity of McAb 3872

Purified preparations of normal serum and malignant tumor effusion fluid were subjected to nondenaturing PAGE and electrophoretically transferred to nitrocellulose using "Western" blotting. After blocking unoccupied protein-binding sites with BSA as described above, 4 lanes of resolved GT proteins were incubated with, respectively, (1) 1:1000 dilution of mouse anti-human GT serum (polyclonal), (2) 1:100 dilution of McAb 3872, (3) 1:1000 dilution of McAb 3872, and (4) 1:1000 dilution of normal human serum (all dilutions in PBS). Following washing to remove unbound antibody, peroxidase-conjugated goat antimouse IgG+IgM in PBS was added to provide a visualizing reagent for the bound antibody. After washing, the sites for anti-GT monoclonal antibody binding were visualized by adding peroxidase-substrate solution (hydrogen peroxide+4-chloro-1-napthol in PBS). The mouse antihuman GT serum bound all forms of GT. McAb 3872 at both dilutions bound onto the GT-II and the higher oligomers and not to GT-I. The normal human serum did not bind any GT proteins.

Assay of Samples from Normal and Cancer Patients with McAb 3872

Protocol

A. Coupling of Antibody 3872 to Gel

Carbodiimide-activated trisacryl gel GF-2000 (Pierce Chem. Co.) is washed twice with distilled $H_2O$ and coupling buffer (0.1M borate, pH 8.5). Monoclonal antibody 3872 (2 mg) in 2 ml of coupling buffer and 2 ml of washed GF-2000 gel are incubated at 4° C. overnight with shaking. Unreacted monoclonal antibody is recovered for reuse and unreacted active sites on the gel are blocked by incubation with 2 ml of 5% BSA in coupling buffer at 4° C. overnight with shaking. The coupled gel is washed with 0.1M citrate, 1.4M NaCl (pH 4.0), 0.1M carbonate, 1.4M NaCl (pH 11.0) and finally CKT buffer (20 mM sodium cacodylate, 150 mM KCl 0.01% Triton X-100). Coupled gel is stored at 4° C. in 5 volumes of 5% BSA, 0.05% sodium azide in CKT buffer. Estimate 1 mg McAb coupled per 1 ml gel based on recovered unbound protein.

B. GT-II Assay Using McAb 3872 Coupled GF-2000 Gel

Twenty-five (25) μl McAb 3872 coupled gel suspension (gel volume, 5 μl) and GT sample are combined in 12×75-mm borosilicate test tube and incubated overnight at 4° C. with shaking. Two ml of cold CKT buffer is added and after settling at 1×g for 5 min, the supernatant is aspirated off. This step is repeated two additional times. Seventy (70) μl of GT substrate is then added (7 μl [$^3$H] UDP-gal 0.5 mM, total input 150,000 dpm (New England Nuclear), 3 μl 0.2M $MnCl_2$, 60 μl CKT buffer, 2 mg OVA (ovalbumin) and the mixture is incubated at 37° C. for 2 hr with shaking. Fifty (50) μl of the reaction mixture is then spotted on 1×1-inch Whatman 3 MM paper and the assay papers are immediately placed in a large volume of 10% TCA for 10 min. This step of contacting with TCA is repeated three times. The assay papers are then washed in 95% ethanol for 10 min followed by a 10-min wash in diethylether. After air-drying, the individual assay papers are placed in scintillation vials, scintillation cocktail added, and the amount of radioactive protein precipitated on the filter paper determined by liquid scintillation counting.

Results

Twenty-nine plasma samples from normal patients and 24 samples of ascites fluid from cancer patients were separately assayed by the above procedure. Activity resulting from the normal plasma samples was ≦1000 cpm, whereas all but three of the ascites samples gave activity above 1000 cpm. A count of 1000 cpm is approximately equivalent to an enzyme activity of 175 picomoles/hr/ml.

Modification of the above-described modes for carrying out the invention that are obvious to those of skill in the fields of immunology, hybridoma technology, cancer diagnosis, biochemistry and related fields are intended to be within the scope of the following claims.

We claim:

1. A monoclonal antibody to galactosyltransferase II that has no measurable cross-reactivity with galactosyltransferase I.

2. The antibody of claim 1 having an affinity of at least about $10^9$ liters per Mole.

3. A monoclonal antibody produced by hybridoma ATCC HB8945.

4. A hybridoma line that produces a monoclonal antibody to galactosyltransferase II that has no measurable cross-reactivity with galactosyltransferase I.

5. The hybridoma line of claim 4 wherein the line is ATCC HB8945.

6. A reagent for use in an immunoassay for galactosyltransferase II comprising the monoclonal antibody of claim 1 bound to a solid support.

7. A reagent for use in an immunoassay for galactosyltransferase II comprising the monoclonal antibody of claim 2 bound to a solid support.

8. A reagent for use in an immunoassay for galactosyltransferase II comprising the monoclonal antibody of claim 3 bound to a solid support.

9. An assay for human cancer comprising:
(a) incubating a sample of body fluid from a patient with the monoclonal antibody of claim 1 bound to a solid support;
(b) removing unbound body fluid from said support;
(c) determining the level of galactosyltransferase activity exhibited by the material bound to the support.

10. An assay for human cancer comprising:
(a) incubating a sample of body fluid from a patient with the monoclonal antibody of claim 2 bound to a solid support;
(b) removing unbound body fluid from said support;
(c) determining the level of galactosyltransferase activity exhibited by the material bound to the support.

11. A assay for human cancer comprising:
(a) incubating a sample of body fluid from a patient with the monoclonal antibody of claim 3 bound to a solid support;
(b) removing unbound body fluid from said support;
(c) determining the level of galactosyltransferase activity exhibited by the material bound to the support.

* * * * *